(12) United States Patent
Blase et al.

(10) Patent No.: US 10,966,739 B2
(45) Date of Patent: Apr. 6, 2021

(54) MEDICAL INSTRUMENT

(71) Applicant: Karl Storz SE & Co. KG, Tuttlingen (DE)

(72) Inventors: Bastian Blase, Berlin (DE); Simon Albrecht, Berlin (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

(21) Appl. No.: 16/781,145

(22) Filed: Feb. 4, 2020

(65) Prior Publication Data
US 2020/0253625 A1 Aug. 13, 2020

(30) Foreign Application Priority Data
Feb. 12, 2019 (DE) ...................... 10 2019 103 489.2

(51) Int. Cl.
*A61B 17/29* (2006.01)
*A61B 17/28* (2006.01)

(52) U.S. Cl.
CPC ........ *A61B 17/282* (2013.01); *A61B 17/2833* (2013.01); *A61B 2017/293* (2013.01); *A61B 2017/2911* (2013.01)

(58) Field of Classification Search
CPC ................ A61B 10/06; A61B 18/1442; A61B 2018/00601; A61B 2018/00952;
(Continued)

(56) References Cited

U.S. PATENT DOCUMENTS 8,142,473 B2   3/2012 Cunningham
9,216,013 B2  12/2015 Scirica et al.
(Continued)

FOREIGN PATENT DOCUMENTS

DE           103 14 828 B3   7/2004
DE    10 2015 103 913 A1    9/2016
(Continued)

OTHER PUBLICATIONS

Search Report, DE 10 2019 103 489.2, dated Jan. 23, 2020 (9 pp.).
Search Report for EP 20155028.2, dated Jun. 18, 2020 (7 pp.).

*Primary Examiner* — Tan-Uyen T Ho
*Assistant Examiner* — Arwa Mostafa
(74) *Attorney, Agent, or Firm* — Eversheds Sutherland (US) LLP

(57) ABSTRACT

The application relates to a medical instrument with a hollow shaft, at the proximal end a handle is arranged, and at the distal end a tool with two jaw parts is arranged, of which at least one jaw part is pivotable, wherein the distal end is configured as a tool tip that can be deflected, and the tool tip is rotatable, wherein the rotation of the tool tip is effected via a first actuation element which is operatively connected at the proximal end to the handle, and wherein the deflection of the tool tip is effected via a second actuation element which is operatively connected to the handle, and wherein the at least one pivotable jaw part is adjustable between a closed position and an open position via a pull/push element. The pull/push element is mounted eccentrically in the tool tip and parallel to the longitudinal axis.

17 Claims, 7 Drawing Sheets

(58) Field of Classification Search
CPC .............. A61B 17/142; A61B 17/2804; A61B 17/2816; A61B 17/282; A61B 17/2841; A61B 17/3201; A61B 2017/003; A61B 2017/00336; A61B 2017/00349; A61B 2017/00353; A61B 2017/0046; A61B 2017/22034; A61B 2017/22035; A61B 2017/22039; A61B 2017/2808; A61B 2017/2902; A61B 2017/2905; A61B 2017/2908; A61B 2017/2927; A61B 2017/2932; A61B 2017/2929; A61B 2017/29; A61B 2017/2938; A61B 2017/294; A61B 2017/2944; A61B 2017/2945; A61B 2017/320766; A61B 2017/32096; A61B 2017/447
See application file for complete search history.

(56) References Cited

U.S. PATENT DOCUMENTS

| | | |
|---|---|---|
| 2008/0147113 A1 | 6/2008 | Nobis et al. |
| 2011/0276084 A1 | 11/2011 | Shelton, IV |

FOREIGN PATENT DOCUMENTS

| | | | | |
|---|---|---|---|---|
| DE | 10 2015 015 655 A1 | 6/2017 | | |
| EP | 0 596 213 A1 | 5/1994 | | |
| EP | 0 596 213 A1 | 11/1994 | | |
| EP | 1637086 A1 * | 3/2006 | ......... | A61B 18/1445 |
| WO | 2019136041 A1 | 7/2019 | | |

* cited by examiner

MEDICAL INSTRUMENT

TECHNICAL FIELD

The invention relates to a medical instrument with a hollow shaft, at the proximal end of which a handle is arranged, and at the distal end of which a tool with two jaw parts is arranged, of which at least one jaw part is pivotable relative to the other jaw part, wherein a distal end region of the shaft that carries the tool is configured as a tool tip that can be deflected with respect to the longitudinal axis of the shaft, and the tool tip is rotatable about the longitudinal axis of the shaft respectively about the longitudinal axis of the tool tip, wherein the rotation of the tool tip about the longitudinal axis of the shaft respectively the longitudinal axis of the tool tip is effected via a first actuation element which is mounted rotatably in the hollow shaft and which is operatively connected at the proximal end to the handle, and wherein the deflection of the tool tip is effected via a second actuation element which is mounted axially displaceably in the hollow shaft and which is operatively connected at the proximal end to the handle, and wherein the at least one pivotable jaw part of the tool is adjustable between a closed position and an open position via a pull/push element which is mounted axially displaceably in the tool tip and which is operatively connected at the proximal end to the handle.

BACKGROUND OF THE INVENTION

Medical instruments for endoscopic surgery generally have a hollow shaft, at the proximal end of which a handle is arranged, and at the distal end of which a tool is arranged that consists of two jaw parts movable relative to each other. The tool, configured as a gripping, holding and/or cutting instrument, can be actuated via the handle. To be able to provide the greatest possible range of action within the often confined working conditions in which the tool is used, many endoscopic instruments are configured such that the tool can be deflected with respect to the longitudinal axis of the shaft and also such that the tool is rotatable about the longitudinal axis of the shaft.

Medical instruments of this kind are known from practice in various designs. To be able to provide the tool tip with the various degrees of freedom relative to the shaft, the various joints and force-transmitting elements often need to be of an extremely complicated structure that also takes up much space.

A medical instrument of the type in question is known from DE 103 14 828 B3, for example.

For the user and patient, however, it would be desirable, on the one hand, for the instrument shaft to have the smallest possible diameter and, on the other hand, for the tool tip to be as short as possible, so as to ensure maximum dexterity in the handling of the instrument.

SUMMARY OF THE INVENTION

Proceeding from this, the object of the invention is to create a medical instrument of the type mentioned at the outset which, while having a simple structure and compact format, ensures the complete mobility of the tool tip.

This object is achieved according to the invention by the fact that the pull/push element for actuation of the at least one pivotable jaw part is mounted eccentrically in the tool tip and parallel to the longitudinal axis of the shaft respectively the longitudinal axis of the tool tip.

Since the pull/push element for actuation of the at least one pivotable jaw part is positioned eccentrically, it is possible to create space for the mechanism for deflection of the tool tip, without increasing the diameter of the shaft and/or of the tool tip.

In order to deflect the tool tip, it is proposed, in a practical embodiment of the invention, that the tool tip is mounted at the distal end of the shaft via a slotted-guide element in such a way as to be deflectable with respect to the longitudinal axis of the shaft.

The invention further proposes that the proximal end of the tool tip is mounted in the slotted-guide element via a hollow pin arranged eccentrically with respect to the longitudinal axis of the shaft and/or the longitudinal axis of the tool tip so as to be rotatable about the longitudinal axis of the shaft and/or about the longitudinal axis of the tool tip. The hollow pin arranged eccentrically with respect to the longitudinal axis of the shaft and/or the longitudinal axis of the tool tip serves at the same time to guide and bear the pull/push element for actuation of the at least one pivotable jaw part, mounted eccentrically in the tool tip.

In a practical embodiment of the invention, it is proposed that the distal end of the shaft is formed bifurcated, having two parallel webs arranged at a distance from each other.

In order to deflect the tool tip mounted in the slotted-guide element, it is proposed according to the invention that the slotted-guide element is mounted between the two webs of the distal end of the shaft via bearing pins so as to be deflectable with respect to the longitudinal axis of the shaft, wherein the bearing pins are mounted in corresponding bearing receptacles of the webs.

According to a preferred embodiment of the invention, the second actuation element mounted in the shaft in order to deflect the tool tip is configured as an axially displaceable pull/push element, which for its part is mounted at the distal end on the slotted-guide element, such that, when a pulling movement is exerted in the proximal direction, the slotted-guide element and therefore also the tool tip mounted in the slotted-guide element are deflected with respect to the longitudinal axis of the shaft.

In order to avoid an excessive deflection of the tool tip with respect to the shaft, it is proposed according to the invention that the deflection of the tool tip with respect to the longitudinal axis of the shaft is limitable via at least one stop element. The at least one stop element is advantageously configured as a pin which is mounted in at least one web of the distal end of the shaft and which engages in a guide track formed in the slotted-guide element.

According to a practical embodiment of the invention, the first actuation element for rotation of the tool tip about the longitudinal axis of the shaft respectively the longitudinal axis of the tool tip is configured as a shank which is mounted rotatably in the shaft and which for its part is coupled at the distal end to the tool tip, wherein the shank is secured at the tool tip via a connection sleeve in order to transmit the rotation of the shank to the tool tip as far as possible without play.

It is further proposed according to the invention that the pull/push element mounted axially displaceably in the tool tip and serving for actuation of the at least one pivotable jaw part of the tool is drivable via a shank which is mounted rotatably in the shaft and which is coupled at the proximal end to the handle.

In order to convert the rotational movement of the shank into an axial movement of the pull/push element, the shank according to the invention is coupled at its distal end to a spindle, wherein the spindle is operatively connected by an external thread to an internal thread in the pull/push element. The external thread of the spindle and the internal thread in the pull/push element effect the conversion of the rotational movement into a purely axial movement.

The shank and the spindle are advantageously coupled to each other via a connection sleeve, in order to transmit the rotation of the shank to the spindle as far as possible without play.

To be able to arrange the shanks inside the shaft in a way that takes up the least possible space, the invention proposes that the shank for rotation of the tool tip and the shank for actuation of the pull/push element are mounted coaxially to each other in the shaft, wherein the shank for rotation of the tool tip is configured as an outer shank, and the shank for actuation of the at least one pivotable jaw part is configured as an inner shank.

The invention further proposes that the shanks are configured as flexible shanks.

According to a preferred embodiment of the invention, it is proposed that a slit extending in the direction of the longitudinal axis of the shaft and reaching up to the distal end of the shaft is formed in a distal end region of the shaft, wherein the slit is formed along that side of the shaft which lies opposite the direction of the deflection of the tool tip, in order to allow the flexible shanks to emerge radially from the shaft during the deflection of the tool tip. The configuration of the shanks as flexible shanks allows the shanks to bulge out from the shaft during the deflection of the tool tip. This bulging-out of the shanks permits a particularly compact and short configuration of the tool tip, since the rotation of the shanks can be transmitted to the tool tip without the need for complicated mechanical conversion mechanisms that increase the overall length. Since the lateral bulging-out of the shanks from the shaft comes into use only at the operating site, the diameter of the medical instrument is not increased by this configuration.

Finally, the invention proposes that the shank for rotation of the tool tip and the spindle for actuation of the at least one pivotable jaw part of the tool are decoupled relative to each other via a radially outwardly acting clamping ring, which is arranged coaxially on the spindle.

BRIEF DESCRIPTION OF THE DRAWINGS

Further features and advantages of the invention will become clear from the attached drawings in which an illustrative embodiment of a medical instrument according to the invention is shown simply by way of example, without limiting the invention to this illustrative embodiment. In the drawings.

DETAILED DESCRIPTION

Figure 1:
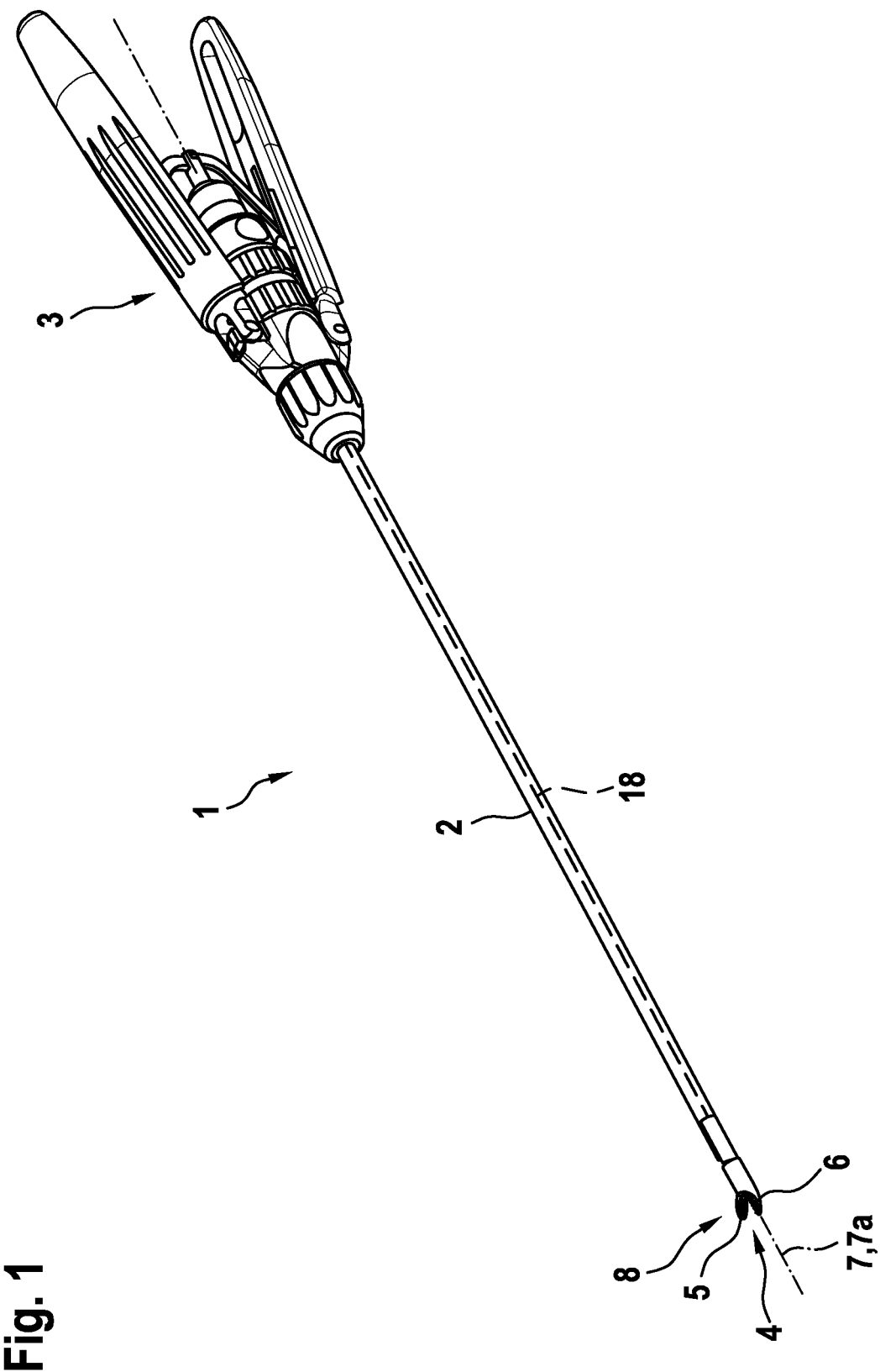
FIG. 1 shows a perspective side view of a medical instrument according to the invention.

FIG. 1 shows a medical instrument 1 with a hollow shaft 2, at the proximal end of which a handle 3 is arranged, and at the distal end of which a tool 4 is arranged consisting of two jaw parts 5, 6 which, in the embodiment described in more detail below, are configured as jaw parts 5 and 6 that are pivotable relative to each other.

In order to afford the tool 4 the greatest possible number of degrees of freedom for the movement relative to the shaft 2, a distal end region of the shaft 2 that carries the tool 4 is configured as a tool tip 8 that is deflectable with respect to the longitudinal axis 7 of the shaft 2. Moreover, the tool 4 is rotatable about the longitudinal axis 7 of the shaft 2 respectively, with the tool tip 8 deflected, about the longitudinal axis 7a of the tool tip 8.

In order to pivot the jaw parts 5 and 6 of the tool 4 relative to each other between a closed position and an open position, an axially displaceable pull/push element 9 is mounted in the tool tip 8, the proximal end of said pull/push element 9 being operatively connected to the handle 3.

The rotation of the tool tip 8 about the longitudinal axis 7 of the shaft 2 respectively the longitudinal axis 7a of the tool tip 8 takes place via a first actuation element 10 mounted rotatably in the hollow shaft 2, whereas the deflection of the tool tip 8 is effected via a second actuation element 11 mounted axially displaceably in the hollow shaft 2. The first actuation element 10 for rotation of the tool tip 8 and the second actuation element 11 for deflection of the tool tip 8 are both operatively connected at the proximal end to the handle 3.

A main problem in the production of medical instruments 1 of this kind is, on the one hand, to maintain all degrees of freedom while ensuring that the diameter of the shaft 2 is as small as possible, and, on the other hand, to make the tool tip 8 as short as possible, so as to ensure maximum dexterity in the handling of the medical instrument 1.

Figure 2:
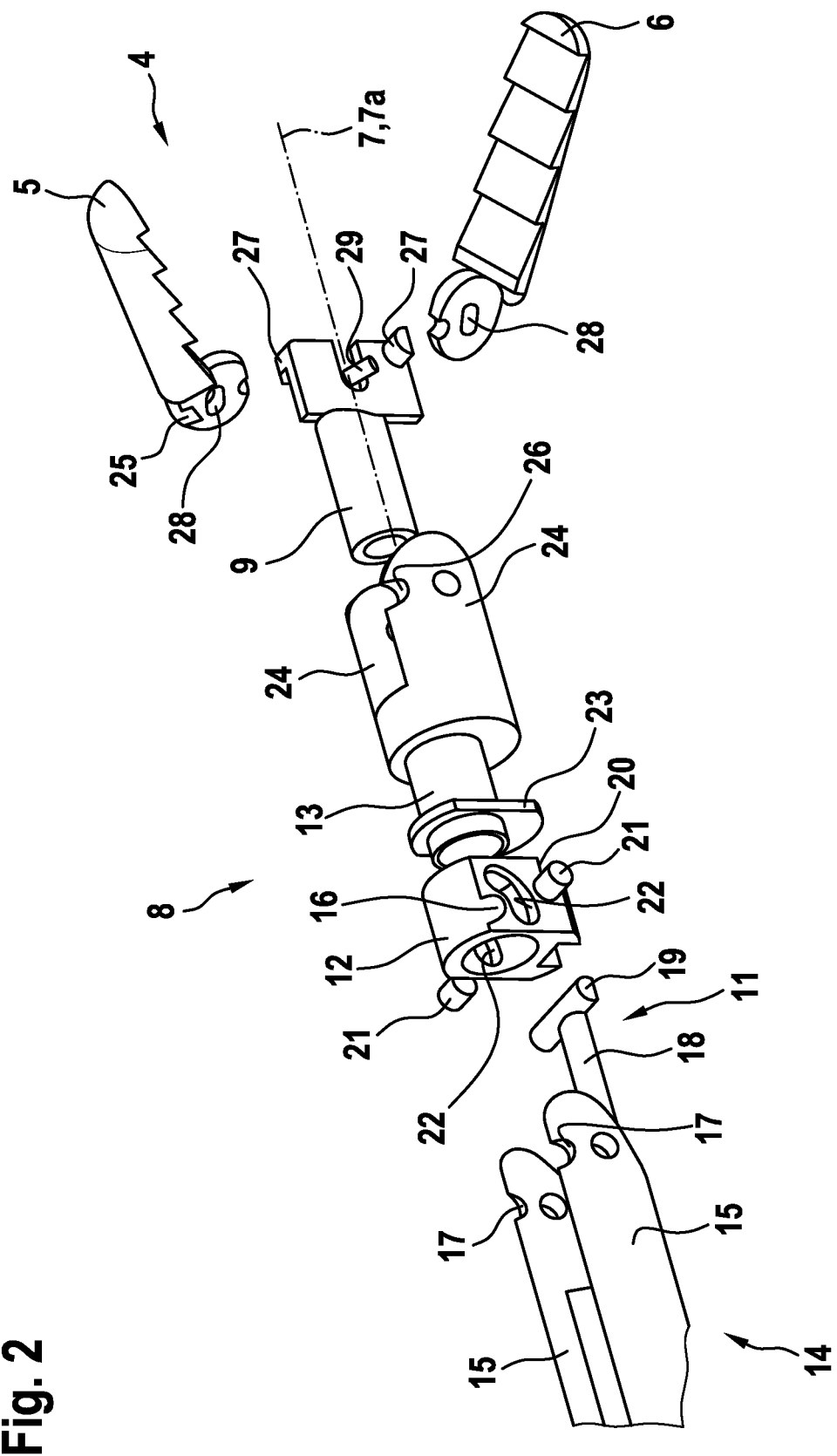
FIG. 2 shows an exploded perspective view of the detail II according to FIG. 1.

In order on the one hand to allow the pull/push element 9 to actuate the pivotable jaw parts 5 and 6 and on the other hand to create space for the mechanism for deflection of the tool tip 8 without increasing the diameter of the shaft 2 and/or of the tool tip 8, it is proposed, as will be seen in particular from FIG. 2, that the pull/push element 9 for actuation of the pivotable jaw parts 5 and 6 is mounted eccentrically in the tool tip 8 and parallel to the longitudinal axis 7 of the shaft 2 respectively the longitudinal axis 7a of the tool tip 8.

Figure 3:
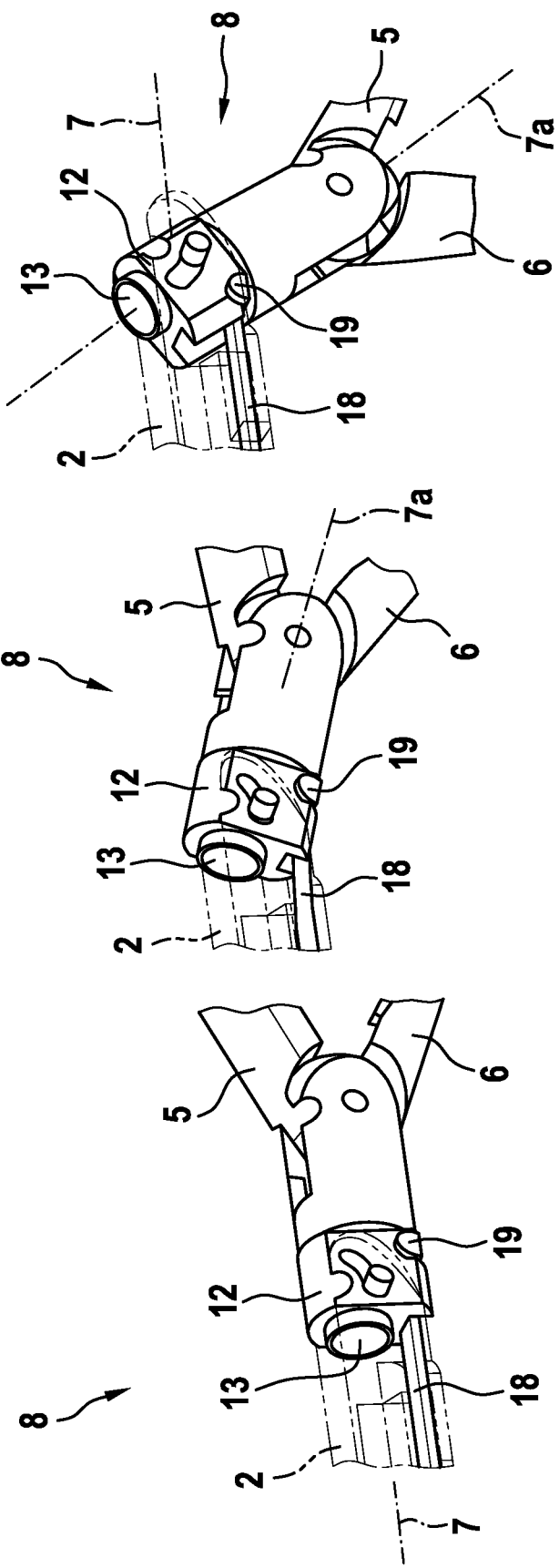
FIG. 3 shows a perspective view of the tool tip in three different working positions.

As will be seen by comparing FIGS. 2 and 3, the tool tip 8 is mounted at the distal end of the shaft 2 via a slotted-guide element 12 in such a way as to be deflectable with respect to the longitudinal axis 7 of the shaft 2, wherein the proximal end of the tool tip 8 is mounted in the slotted-guide element 12 so as to be rotatable about the longitudinal axis 7 of the shaft 2 respectively about the longitudinal axis 7a of the tool tip 8 via a hollow pin 13 arranged eccentrically with respect to the longitudinal axis 7 of the shaft 2 respectively the longitudinal axis 7a of the tool tip 8. The hollow pin 13 arranged eccentrically with respect to the longitudinal axis 7 of the shaft 2 respectively the longitudinal axis 7a of the tool tip 8 serves at the same time to guide and bear the pull/push element 9, mounted eccentrically in the tool tip, for actuation of the pivotable jaw parts 5 and 6.

To receive the slotted-guide element 12 carrying the tool tip 8, the bifurcated distal end 14 of the shaft 2 has two parallel webs 15 arranged at a distance from each other.

The slotted-guide element 12 itself is mounted between the two webs 15 of the distal end 14 of the shaft 2 via bearing pins 16 so as to be deflectable with respect to the longitudinal axis 7 of the shaft 2, wherein the bearing pins 16 are mounted in corresponding bearing receptacles 17 of the webs 15.

The force that has to be applied in order to pivot the tool tip 8 reduces by virtue of the fact that the points at which the bearing pins 16 and the second actuation element 11 engage eccentrically on the slotted-guide element 12 are spaced relatively far apart from each other.

In order to deflect the tool tip 8, the second actuation element 11 mounted in the shaft 2 is configured, as can be seen from FIGS. 2 and 3, as an axially displaceable pull/push element 18, which is mounted at the distal end on the slotted-guide element 12. The distal end of the pull/push element 18 is T-shaped, such that the transverse web 19 of the T-shaped pull/push element 18, forming the distal end of the pull/push element 18 and extending transversely to the longitudinal axis 7 of the shaft 2, is mounted in a bearing receptacle 20 of the slotted-guide element 12, wherein the T-shaped transverse web 19 is advantageously mounted rotatably in the bearing receptacle 20, so as to be able to compensate a possible angular offset during a deflection of the tool tip 8.

When the pull/push element 18 is drawn back in the proximal direction, the slotted-guided element 12, mounted pivotably in the bearing receptacles 17 of the webs 15 of the distal end 14 of the shaft 2 via the bearing pins 16, and the tool tip 8, mounted in the slotted-guide element 12, are pivoted with respect to the longitudinal axis 7 of the shaft, as is shown schematically in FIG. 3.

In order to avoid an excessive deflection of the tool tip 8 with respect to the shaft 2 upon actuation of the pull/push element 18, the deflection of the tool tip 8 with respect to the longitudinal axis 7 of the shaft 2 is limitable via at least one stop element. In the embodiment shown, the at least one stop element is configured as a pin 21 which is mounted in at least one web 15 of the distal end 14 of the shaft 2 and which engages in a guide track 22 formed in the slotted-guide element 12.

The bearing of the pins 21 in the webs 15 of the distal end 14 of the shaft 2, and also in the guide tracks 22 formed in the slotted-guide element 12, additionally prevents the slotted-guide element 12 from being lifted out of the bearing receptacles 17, in particular during the deflection of the tool tip 8.

The mechanism for pivoting the tool tip 8 moreover comprises a cover disk 23 which is mounted on the pin 13 of the tool tip 8, distally in front of the slotted-guide element 12, and which distally closes the bearing receptacle 20 of the slotted-guide element 12 when the transverse web 19 of the pull/push element 18 is inserted, in order to prevent the transverse web 19 of the pull/push element 18 from accidentally escaping from the bearing receptacle 20.

As will be seen from FIGS. 2 and 3, it is only possible by means of the parallel and eccentric bearing of the pull/push element 9 for actuation of the jaw parts 5 and 6 possible, that the mechanism for pivoting the tool tip 8 can also be arranged within a very confined space in the transition region from the shaft 2 to the tool tip 8, without increasing the external diameter of the shaft 2 and of the tool tip 8.

The adjustment of the pivotable jaw parts 5 and 6 of the tool 4 between a closed position and an open position is effected, as can be seen from FIG. 2, via the pull/push element 9 mounted axially displaceably in the tool tip 8.

In order to receive the pull/push element 9 and to bear the pivotable jaw parts 5 and 6, the bifurcated distal end of the tool tip 8 has two parallel webs 24 arranged at a distance from each other. The jaw parts 5 and 6 each have an integrally formed bearing pin 25 via which the respective jaw part 5 or 6 is mounted pivotably in a corresponding bearing receptacle 26 in one of the webs 24. The coupling of the jaw parts 5 and 6 to the pull/push element 9 is effected via two bearing pins 27 formed at the distal end of the pull/push element 9, wherein each bearing pin 27 engages respectively in a recess 28 in the proximal end of a jaw part 5 or 6.

By virtue of the positionally fixed bearing of the jaw parts 5 and 6 at the tool tip 8 via the bearing pins 25 of the jaw parts 5 and 6 arranged in the bearing receptacles 26, the jaw parts 5 and 6 are pivoted relative to each other between an open position and a closed position during the axial displacement of the pull/push element 9 in the direction of the longitudinal axis 7a of the tool tip 8.

The movement clearance of the pull/push element 9 distally in the axial direction is limited by an additional pin 29, which is mounted in a fixed position in the webs 24 of the tool tip 8 and against which the pull/push element 9 abuts as stop element during the movement in the axial direction.

As an alternative to the embodiment of the tool tip 8 and of the slotted-guide element 12 as shown in particular in FIGS. 2 and 3, the proximal end of the hollow pin 13 of the tool tip 8 and the proximal end of the slotted-guide element 12 can each be configured with a chamfer as a run-on bevel. Such a chamfer configured as a run-on bevel has the effect that, when the medical instrument 1 is drawn back into a trocar sleeve, the chamfer runs up against the inner wall of the trocar sleeve and the tool tip 8 is thus transferred back again to a fully straight position, extending in the direction of the longitudinal axis 7 of the shaft 2, if the tool tip 8 was still slightly deflected upon retraction of the medical instrument 1 into the trocar sleeve.

Figure 4:
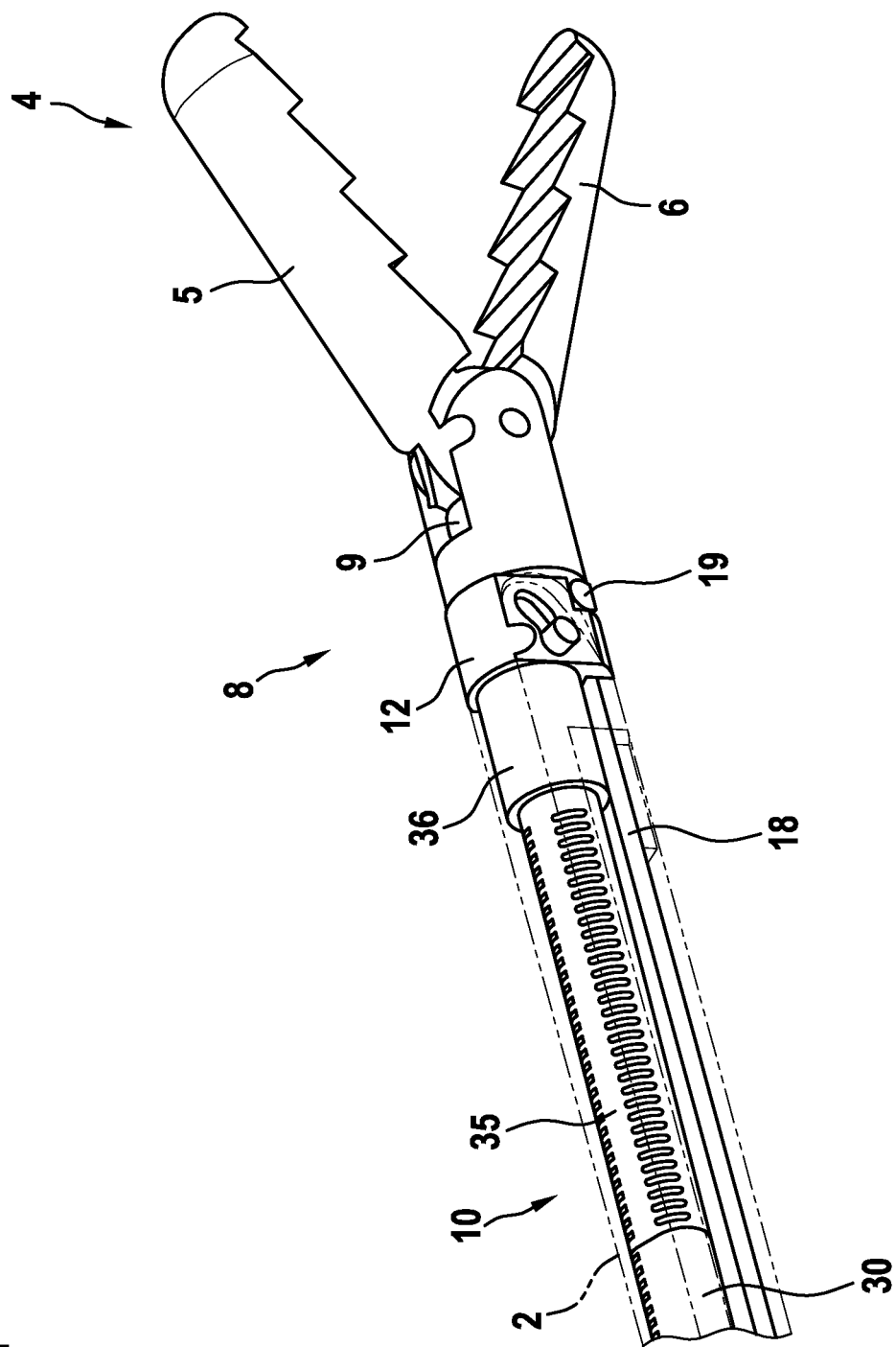
FIG. 4 shows a partially sectioned perspective view of the distal end of the shaft of the medical instrument according to the invention.
Figure 5:
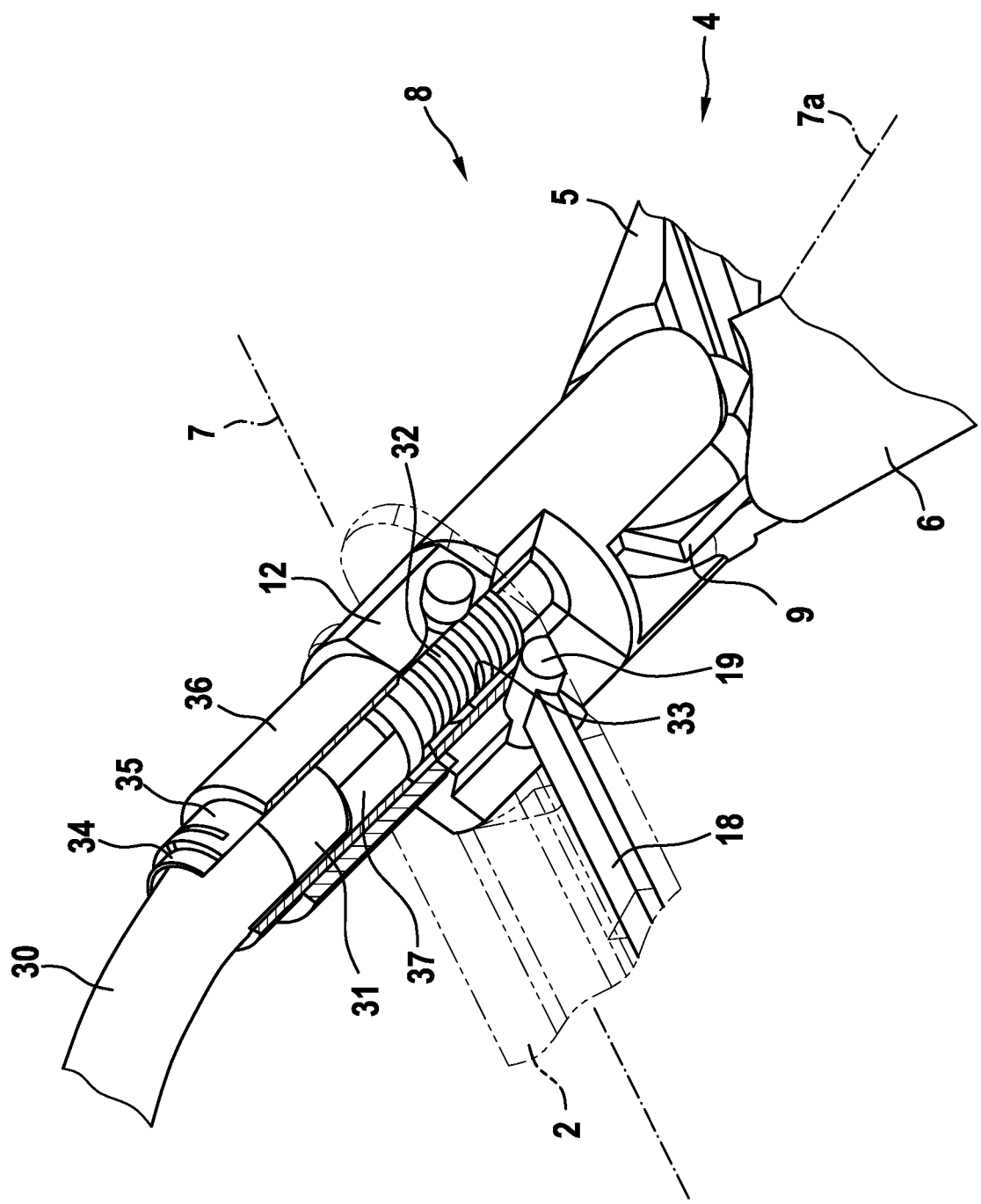
FIG. 5 shows an enlarged and partially sectioned detail of the view according to FIG. 4, with a deflected tool tip.
Figure 6:
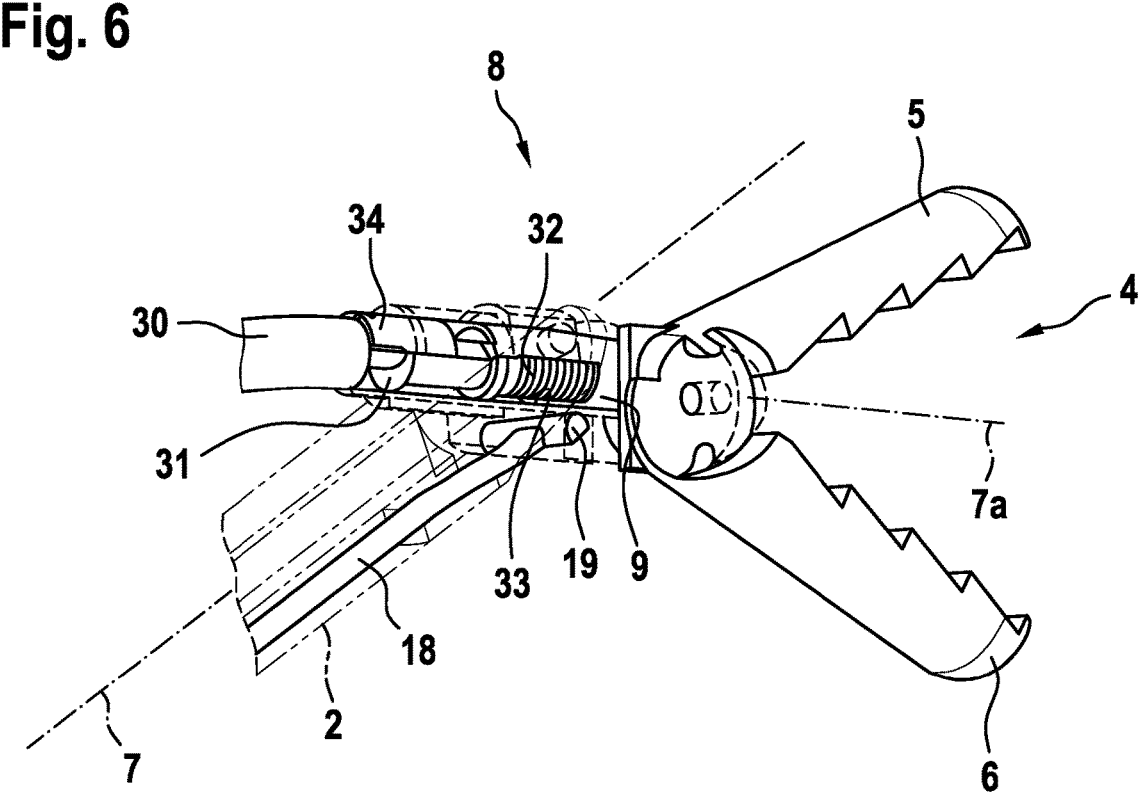
FIG. 6 shows a partial detail of the view according to FIG. 5, depicting the mechanism for actuation of the jaw parts.

The pull/push element 9 mounted axially displaceably in the tool tip 8, for actuation of the jaw parts 5 and 6, is coupled to the handle 3 via a shank 30 which is mounted rotatably in the shaft 2 and which at the proximal end is coupled to the handle 3 and at the distal end is operatively connected to the pull/push element 9, as can be seen in FIGS. 4 to 6.

In order to convert the rotational movement of the shank 30 into an axial movement of the pull/push element 9, the shank 30 is coupled at its distal end to a spindle 31, wherein the spindle 31 is operatively connected by an external thread 32 to an internal thread 33 in the pull/push element 9. The external thread 32 of the spindle 31 on the one hand and the internal thread 33 in the pull/push element 9 on the other hand effect the conversion of the rotational movement into a purely axial movement.

The shank 30 and the spindle 31 are advantageously coupled to each other via a connection sleeve 34, in order to transmit the rotation of the shank 30 to the spindle 31 as far as possible without play.

Figure 7:
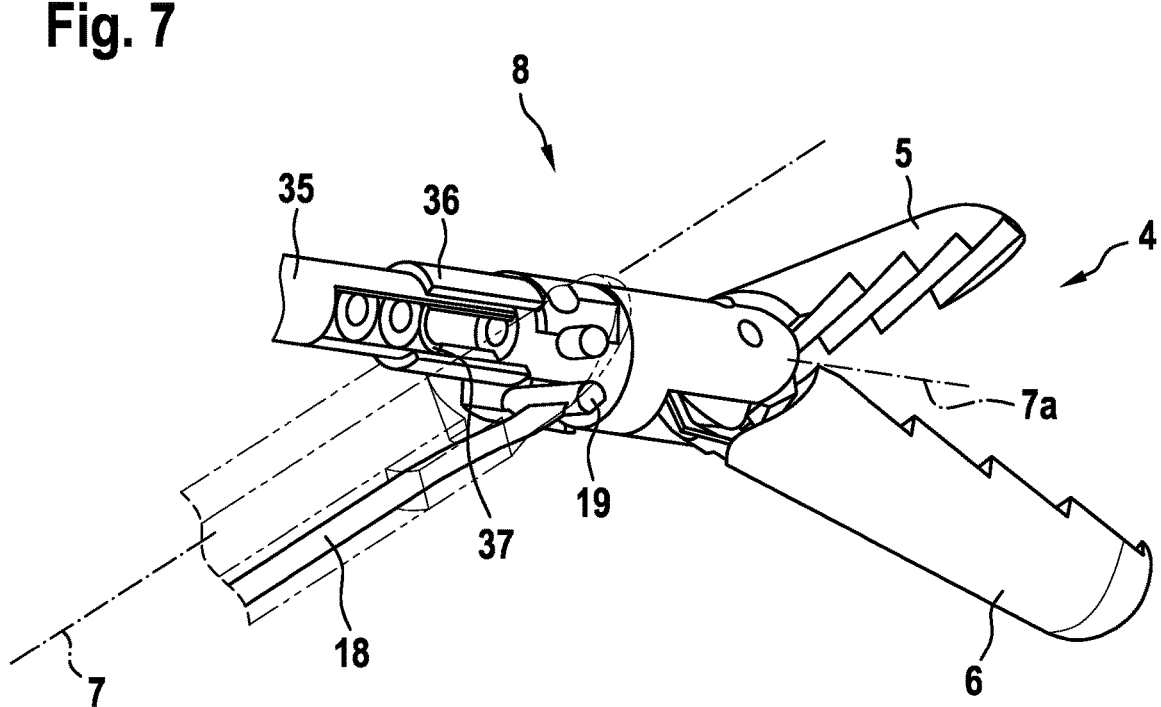
FIG. 7 shows a partial detail of the view according to FIG. 5, depicting the mechanism for rotation of the tool tip.

According to the embodiment shown, the first actuation element 10 for rotating the tool tip 8 about the longitudinal axis 7 of the shaft 2 respectively the longitudinal axis 7a of the tool tip 8 is configured as a shank 35 which is mounted rotatably in the shaft 2 and which for its part is coupled at the distal end to the tool tip 8, wherein the shank 35 is secured at the tool tip 8 via a connection sleeve 36 in order to transmit the rotation of the shank 35 to the tool tip 8 as far as possible without play, as can be seen from FIGS. 4, 5 and 7.

To be able to arrange the shanks 30 and 35 inside the shaft 2 in a way that takes up the least possible space, the shank 35 for rotation of the tool tip 8 and the shank 30 for actuation of the pull/push element 9 are mounted coaxially to each other in the shaft 2, wherein the shank 35 for rotation of the tool tip 8 is configured as an outer shank, and the shank 30 for actuation of the pivotable jaw parts 5 and 6 is configured as an inner shank, as can be seen from FIGS. 4 and 5.

As can be seen from FIG. 5, at the distal end of the shank 35 for rotation of the tool tip 8, a radially outwardly acting clamping ring 37 is arranged coaxially on the spindle 31 in order to decouple the movement of the spindle 31 and the movement of the shank 35 from each other.

Figure 8:
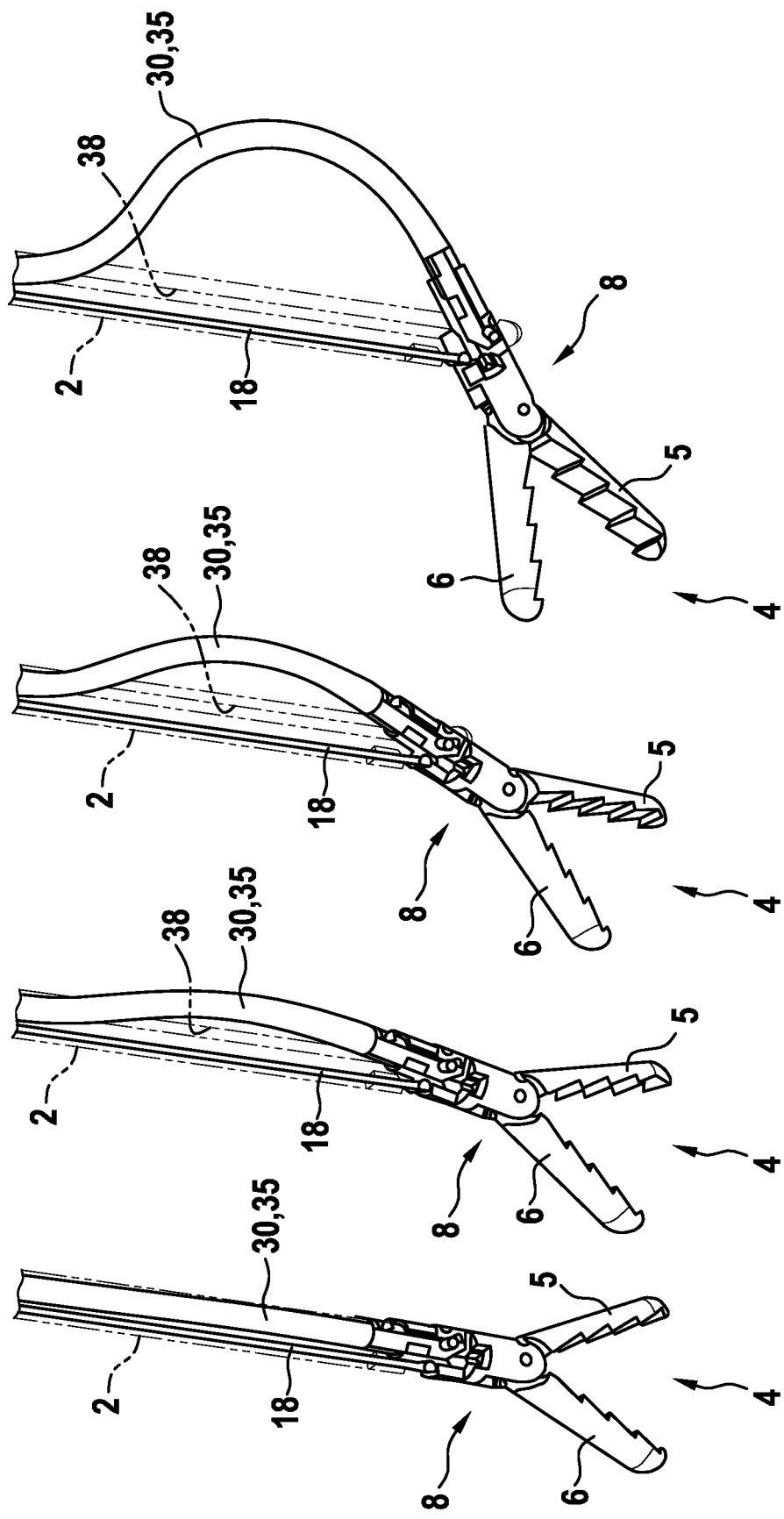
FIG. 8 shows a side view of the distal end of the shaft, depicting the tool tip in different working positions.

FIG. 8 finally shows that a slit 38 extending in the direction of the longitudinal axis 7 of the shaft 2 and reaching up to the distal end 14 of the shaft 2 is formed in a distal end region of the shaft 2. This slit 38 is formed along that side of the shaft 2 which lies opposite the direction of the deflection of the tool tip 8, in order to allow the flexible shanks 30 and 35 to emerge radially from the shaft 2 during the deflection of the tool tip 8. This bulging-out of the shanks 30 and 35 permits a particularly compact and short configuration of the tool tip 8, since the rotation of the shanks 30 and 35 can be transmitted to the tool tip 8 without the need for complicated mechanical conversion mechanisms that increase the overall length. Since the lateral bulging-out of the shanks 30 and 35 from the shaft 2 comes into use only at the operating site, the diameter of the medical instrument 1 is not increased by this configuration.

A medical instrument 1 configured in the manner described above is characterized by the fact that, while having a simple structure and compact format, it ensures the complete mobility of the tool tip 8.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS 1 medical instrument
2 shaft
3 handle
4 tool
5 jaw part
6 jaw part
7 longitudinal axis (of the shaft)
7a longitudinal axis (of the tool tip)
8 tool tip
9 pull/push element
10 first actuation element
11 second actuation element
12 slotted-guide element
13 pin
14 distal end (of the shaft)
15 web
16 bearing pin
17 bearing receptacle
18 pull/push element
19 transverse web
20 bearing receptacle
21 pin (stop element)
22 guide track
23 cover disk
24 web
25 bearing pin
26 bearing receptacle
27 bearing pin
28 recess
29 pin
30 shank
31 spindle
32 external thread
33 internal thread
34 connection sleeve
35 shank
36 connection sleeve
37 clamping ring
38 slit

We claim:

1. A medical instrument comprising a hollow shaft, at the proximal end of which a handle is arranged, and at the distal end of which a tool with two jaw parts is arranged, of which at least one jaw part is pivotable relative to the other jaw part, wherein a distal end region of the shaft that carries the tool is configured as a tool tip that can be deflected with respect to the longitudinal axis of the shaft, and the tool tip is rotatable about the longitudinal axis of the shaft or about the longitudinal axis of the tool tip, wherein the rotation of the tool tip about the longitudinal axis of the shaft or the longitudinal axis of the tool tip is effected via a first actuation element which is mounted rotatably in the hollow shaft and which is operatively connected at the proximal end to the handle, and wherein the deflection of the tool tip is effected via a second actuation element which is mounted axially displaceably in the hollow shaft and which is operatively connected at the proximal end to the handle, and wherein the at least one pivotable jaw part of the tool is adjustable between a closed position and an open position via a pull/push element which is mounted axially displaceably in the tool tip and which is operatively connected at the proximal end to the handle, wherein
the pull/push element for actuation of the at least one pivotable jaw part is mounted eccentrically in the tool tip and parallel to the longitudinal axis of the shaft or the longitudinal axis of the tool tip.

2. The medical instrument according to claim 1, wherein the tool tip is mounted at the distal end of the shaft via a slotted-guide element in such a way as to be deflectable with respect to the longitudinal axis of the shaft.

3. The medical instrument according to claim 2, wherein the proximal end of the tool tip is mounted in the slotted-guide element via a hollow pin arranged eccentrically with respect to the longitudinal axis of the shaft respectively the longitudinal axis of the tool tip so as to be rotatable about the longitudinal axis of the shaft or about the longitudinal axis of the tool tip.

4. The medical instrument according to claim 2, wherein the distal end of the shaft is formed bifurcated, having two parallel webs arranged at a distance from each other.

5. The medical instrument according to claim 4, wherein the slotted-guide element is mounted between the two webs of the distal end of the shaft via bearing pins so as to be deflectable with respect to the longitudinal axis of the shaft, wherein the bearing pins are mounted in corresponding bearing receptacles of the webs.

6. The medical instrument according to claim 2, wherein the second actuation element mounted in the shaft in order to deflect the tool tip is configured as an axially displaceable pull/push element, which is mounted at the distal end on the slotted-guide element.

7. The medical instrument according to claim 2, wherein the deflection of the tool tip with respect to the longitudinal axis of the shaft is limitable via at least one stop element.

8. The medical instrument according to claim 7, wherein the at least one stop element is configured as a pin which is mounted in at least one web of the distal end of the shaft and which engages in a guide track formed in the slotted-guide element.

9. The medical instrument according to one claim 1, wherein the first actuation element for rotation of the tool tip about the longitudinal axis of the shaft or the longitudinal axis of the tool tip is configured as a shank which is mounted rotatably in the shaft and which is coupled at the distal end to the tool tip.

10. The medical instrument according to claim 9, wherein the shank is secured at the tool tip via a connection sleeve.

11. The medical instrument according to claim 10, wherein the pull/push element mounted axially displaceably in the tool tip and serving for actuation of the at least one pivotable jaw part of the tool is drivable via a shank which is mounted rotatably in the shaft and which is coupled at the proximal end to the handle.

12. The medical instrument according to claim 11, wherein the shank is coupled at its distal end to a spindle, wherein the spindle is operatively connected by an external thread to an internal thread in the pull/push element, in order to convert the rotational movement of the shank into an axial movement of the pull/push element.

13. The medical instrument according to claim 12, wherein the shank and the spindle are coupled to each other via a connection sleeve.

14. The medical instrument according to claim 11, wherein the shank for rotation of the tool tip and the shank for actuation of the pull/push element are mounted coaxially to each other in the shaft.

15. The medical instrument according to claim 11, wherein the shank and the shank are both configured as flexible shanks.

16. The medical instrument according to claim 15, wherein a slit extending in the direction of the longitudinal axis of the shaft and reaching up to the distal end of the shaft is formed in a distal end region of the shaft, wherein the slit is formed along that side of the shaft which lies opposite the direction of the deflection of the tool tip, in order to allow the shanks to emerge radially from the shaft during the deflection of the tool tip.

17. The medical instrument according to claim 12, wherein the shank for rotation of the tool tip and the spindle for actuation of the at least one pivotable jaw part of the tool are decoupled relative to each other via a radially outwardly acting clamping ring, which is arranged coaxially on the spindle.

* * * * *